(12) United States Patent
Bui-Khac et al.

(10) Patent No.: US 6,452,024 B1
(45) Date of Patent: Sep. 17, 2002

(54) PROCESS FOR EXTRACTION AND PURIFICATION OF PACLITAXEL FROM NATURAL SOURCES

(75) Inventors: Trung Bui-Khac, Montréal; Nicolas Dupuis, Laval, both of (CA)

(73) Assignee: Chaichem Pharmaceuticals International, Laval (CA)

( * ) Notice: Subject to any disclaimer, the term of this patent is extended or adjusted under 35 U.S.C. 154(b) by 0 days.

(21) Appl. No.: 09/580,362

(22) Filed: May 26, 2000

(30) Foreign Application Priority Data

Feb. 22, 2000 (CA) ............................................. 2299149

(51) Int. Cl.[7] ........................................... C07D 305/14
(52) U.S. Cl. ....................................................... 549/510
(58) Field of Search ......................................... 549/510

(56) References Cited

U.S. PATENT DOCUMENTS

| | | |
|---|---|---|
| 4,857,653 A | 8/1989 | Colin et al. |
| 4,924,011 A | 5/1990 | Denis et al. |
| 5,015,744 A | 5/1991 | Holton |
| 5,019,504 A | 5/1991 | Christen et al. |
| 5,175,315 A | 12/1992 | Holton |
| 5,200,534 A | 4/1993 | Rao |
| 5,279,949 A | 1/1994 | Nair |
| 5,312,740 A | 5/1994 | Saito et al. |
| 5,322,779 A | 6/1994 | Strobel et al. |
| 5,336,785 A | 8/1994 | Holton |
| 5,367,086 A | 11/1994 | Rao |
| 5,380,916 A | 1/1995 | Rao |
| 5,384,399 A | 1/1995 | Holton |
| 5,405,972 A | 4/1995 | Holton et al. |
| 5,440,055 A | 8/1995 | Castor ........................ 549/510 |
| 5,445,809 A | 8/1995 | Strobel et al. |
| 5,451,392 A | 9/1995 | Strobel et al. |
| 5,470,866 A | 11/1995 | Kingston et al. |
| 5,475,120 A | 12/1995 | Rao |
| 5,478,736 A | 12/1995 | Nair |
| 5,480,639 A | 1/1996 | Elsohly et al. |
| 5,508,447 A | 4/1996 | Magnus |
| 5,516,676 A | 5/1996 | Hanson et al. |
| 5,530,020 A | 6/1996 | Gunawardana et al. |
| 5,594,157 A | 1/1997 | Gunawardana et al. |
| 5,614,645 A | 3/1997 | Kingston et al. |
| 5,616,330 A | 4/1997 | Kaufman et al. |
| 5,618,538 A | 4/1997 | Elsohly et al. |
| 5,618,952 A | 4/1997 | Holton et al. |
| 5,637,484 A | 6/1997 | Yukimune et al. |
| 5,654,448 A | 8/1997 | Pandey et al. |
| 5,665,576 A | 9/1997 | Cino et al. |
| 5,670,673 A | 9/1997 | Rao |
| 5,675,025 A | 10/1997 | Sisti et al. |
| 5,679,807 A | 10/1997 | Murray et al. |
| 5,684,169 A | 11/1997 | Hamada et al. |
| 5,693,666 A | 12/1997 | Chen et al. |
| 5,703,247 A | 12/1997 | Kingston et al. |
| 5,719,265 A | 2/1998 | Mongelli et al. |
| 5,739,016 A | 4/1998 | Hanson et al. |
| 5,739,359 A | 4/1998 | Kingston et al. |
| 5,744,333 A | 4/1998 | Cociancich et al. ........ 435/123 |
| 5,750,737 A | 5/1998 | Sisti et al. |
| 5,756,536 A | 5/1998 | Chen et al. |
| 5,760,251 A | 6/1998 | Gao et al. |
| 5,760,252 A | 6/1998 | Holton et al. |
| 5,767,297 A | 6/1998 | Mandai et al. |
| 5,770,745 A | 6/1998 | Swindell et al. |
| 5,773,629 A | 6/1998 | Yang et al. |
| 5,780,653 A | 7/1998 | Tao et al. |
| 5,795,909 A | 8/1998 | Shashoua et al. |
| 5,969,165 A | 10/1999 | Liu |

FOREIGN PATENT DOCUMENTS

CA 2072400 1/1993 ......... C07D/305/14

OTHER PUBLICATIONS

Journal of Liquid Chromatography, 12(11), 2117–2132, (1989) Keith M. Witherup et al, "High performance liquid chromatographic separation of taxol and related compounds from taxus brevifolia", Program Resources Inc., Maryland, USA, pp. 2117–2132.
Wani et al., J. Am. Chem. Soc., 1971: 93: 2325–2327.
Kingston et al., J. Nat. Prod. 1982: 45: 466–470.
Senilh et al., J. Nat. Prod., 1984, 47: 131–137.
Huang et al., J. Nat. Prod., 1986, 49: 665–669.
Vidensek et al., J. Nat. Prod., 1990: 53: 1609–1610.
Blume, E., Natl. Cancer Inst., 1991: 83: 1054–1056.
Rowinski et al., Pharmacol. Ther., 1991; 52: 35–84.
Miller et al., J. Org. Chem., 1981; 46: 1469.
McLaughlin et al., J. Nat. Prod., 1981; 44: 312–319.
Fett–Neto et al., Bio/Technology, 1992; 10: 1572–1575.
Kingston, Pharmacol. Ther., 1991: 52: 1–34.
Kelsey et al., J. Nat. Prod., 1992: 55: 912–917.
Wheeler et al., J. Nat. Prod., 1992: 55: 432–440.

*Primary Examiner*—T. A. Solola (57) ABSTRACT

A process for the extraction and purification of Paclitaxel from a natural source of taxanes, comprising extracting Paclitaxel with an organic solvent from a natural source of taxanes, and treating the raw material with a base or an acid to obtain a biomass by precipitation. The biomass is isolated and dried, and resin and natural pigments are removed. The biomass is then dissolved in acetone and at least one non-polar solvent is added, until a Paclitaxel-enriched oily phase is obtained. The Paclitaxel-enriched oily phase is then treated with a base or an acid to obtain a second biomass, which is recovered by precipitation and dried. A solution of the second biomass in a volatile solvent is chromatographically purified at least once and crystallized.

19 Claims, 3 Drawing Sheets

PROCESS FOR EXTRACTION AND PURIFICATION OF PACLITAXEL FROM NATURAL SOURCES

TECHNICAL FIELD OF THE INVENTION

The present invention relates to an easy and quick process for the extraction and purification of Paclitaxel from natural sources. In comparison to the prior processes known in the art, this process is particularly economical because it has a limited number of steps and a reduced amount of losses during the purification.

PRIOR ART

The first work concerning Paclitaxel, also called Taxol™ or Pacitaxeline™, started in the United States in the 1960's, when the National Cancer Institute began a program for selecting plant extracts having activities against cancerous tumours, or anti-neoplasic activities.

From 1960 to 1981, more than 110,000 composites were extracted from 35,000 species of plants and were isolated and tested (Blume E. J. Natl. Cancer Inst. 1991; 83: 1054–1056).

Yew is part of the plants that were selected and tested, and the first extract from yew barks (*Taxus brevifolia* Nutt) coming from the west coast of the United States (Oregon) was obtained by Wani et al (Wani et al, J. Am. Chem. Soc., 1971; 93:2325–2327). The crude extract of these barks demonstrated a cytotoxic activity against leukaemic cells and an inhibiting action against a variety of tumours.

A couple of years later, the active compound of the extract was isolated. This active compound has been given Paclitaxel as generic name, and its molecular structure has been determined by X-ray crystallography and by 1H-NMR spectrum (Wani et al. J. Am. Chem. Soc. 1971; 93:2325–2327).

Since that time, studies on the effect of Paclitaxel towards cancerous tumours in-vitro and in-vivo have been carried out and the positive results that were obtained have lead to classify this active compound as one of the promising drugs for the treatment of ovarian cancer and breast cancer (Rowinski et al. Pharmacol. Ther. 1991; 52: 35–84). By the way, the use of Paclitaxel for the treatment of different cancers has been approved by the Food and Drug Administration since 1992.

The first variety of yew that was used to produce Paclitaxel, was *Taxus brevifolia*, but other varieties found in different regions of the earth have also been tested. They consist of *Taxus baccata, Taxus canadensis, Taxus wallichiana, Taxus yunnanensis, Taxus densiformis, Taxus hicksii, Taxus wardii, Taxus cuspidata, Taxus capitata, Taxus brownii* (Miller et al. J. Org. Chem. 1981; 46: 1469; McLaughlin et al. J. Nat. Prod. 1981; 44: 321; Kingston et al. J. Nat. Prod 1982; 45: 466; Senilh et al. J. Nat. Prod. 1984; 47: 131–137; Huang et al. J. Nat. Prod. 1986; 49: 665–669; Fett-Neto et al. Bio/Technology 1992; 10: 1572–1575).

All these species contain Paclitaxel, but in very limited amounts—about 0.0004 to 0.008%—(Kingston, Pharmacol. Ther. 1991; 52: 1–34). This low concentration of Paclitaxel makes its extraction and purification very costly because it takes time and it generally calls for repeated chromatographies.

The low concentration of Paclitaxel in all the varieties of yew produces a huge impact on the environment. To extract 1 kg of Paclitaxel from *Taxus brevifolia* barks, one needs to cut down around 3000 grown trees to get 10,000 kg of bark. The obtained quantity (1 kg) of Paclitaxel permits to treat about 500 patients but the number of patients suffering from cancer is as high as hundreds of thousands. Replanting the trees will never meet the urgent demand of Paclitaxel for human needs, because of their slow growth (Vidensek et al. J. Nat. Prod. 1990; 53: 1609–1610; Kelsey et al. J. Nat. Prod. 1992; 55: 912–917; Wheeler et al. J. Nat. Prod 1992; 55: 432–440).

Numerous processes for extracting and purifying Paclitaxel have been proposed. For example, Wani et al. (Wani et al. J. Am. Chem. Soc, 1971; 93: 2325–2327) have proposed a process for extraction of Paclitaxel from the barks of yew of the United States' west coast (*Taxus brevifolia*) comprising a treatment of the barks with alcohol followed by a few steps of purification by chromatography.

Miller et al. (1981) have extracted Paclitaxel from the *Taxus wallichiana* Zucc by a the following process:
1) extraction from the plant and concentration of the extract;
2) fat removal by separation of water and hexane;
3) extraction with chloroform and concentration;
4) first purification by chromatography in a first silica column;
5) second purification by chromatography in a second silica column;
6) a first countercurrent distribution;
7) a second countercurrent distribution;
8) preparative HPLC chromatography.

Senilh et al. (1984) have isolated Paclitaxel (or Taxol™ A: 0.0165%), Cephalomannine (or Taxol™ B: 0.0064%) and other compounds from barks of the *Taxus baccata* by the following process:
1) extraction with alcohol and concentration;
2) separation of water and dichloromethane;
3) filtration chromatography;
4) chromatography in a silica column;
5) alumina chromatography;
6) chromatography in a medium pressure silica column;
7) HPLC chromatography.

For other analog, two or three other column chromatography treatments followed by a preparative HPLC chromatography are necessary.

Another process used by Polysciences Inc. comprises the following steps:
1) dried ground barks are treated with methanol or ethanol and the obtained extract is concentrated to remove the alcohol,
2) the concentrate is then treated with dichloromethane and the obtained solvent extract is concentrated to yield a powder,
3) the powder is dissolved with a mixture of acetone and ligroin (1:1) and filtered to remove insoluble matter,
4) the organic phase which contains Paclitaxel is concentrated, dissolved in 30% of ligroin, and applied to a column of Florisil®,
5) the Paclitaxel fraction from the column is purified by double crystallization,
6) the so obtained crystalline Paclitaxel is subjected to chromatography on a silica column. The Paclitaxel is separated from the other taxanes (related analogs, cephalomannine, etc.) in this step,
7) the purified Paclitaxel obtained from the previous step is crystallized twice, and 8) unseparated mixtures and mother liquors are recycled through the silica column to obtain additional amounts of pure Paclitaxel.

Of course, there are other processes for purifying Paclitaxel from natural sources, as is explained in the following references:

Kingston et al., who disclose new taxanes obtained from *Taxus brevifolia* (J. Nat. Prod. 1982; 45: 466–470); and Witherup et al., who disclose a method for the separation of Paclitaxel and related compounds from *Taxus brevifolia* (J. Liq. Chrom. 1989; 12: 2117–2132).

U.S. Pat. No. 5,279,949 issued to Nair in 1994 discloses the use of tissue from ornamental yew (Taxus×media *Hicksii*) for Paclitaxel purification. In this patent:

1) fresh needles are extracted with 70% alcohol,
2) the extract is decolorized with charcoal and filtered,
3) the filtered extract is concentrated to remove most of the organic solvent,
4) the aqueous concentrate is centrifuged to separate the solids which contain Paclitaxel,
5) the solids are then subjected to a first normal phase silica chromatography,
6) the obtained crude Paclitaxel fraction is subjected to a second, low pressure silica chromatography; and
7) final purification is carried out in a reverse phase column.

U.S. Pat. No. 5,654,448 issued to Pandey et al., discloses a process for extraction and purification of Paclitaxel from barks of *Taxus brevifolia*. In this process:

1) the barks are treated thrice with methanol, each extraction being performed over a period of 5 days, the so-obtained extract being then concentrated;
2) the methanol concentrate is separated to obtain methylene chloride and water and the methylene chloride extract is evaporated to dryness, the solid residue containing the Paclitaxel amounting to about 1.8–2.2% w/w;
3) the solid residue is dissolved in acetone and mixed with one volume of hexane to remove polar impurities, and the mixture is evaporated to ⅓ of its volume;
4) the acetone/hexane residue is added drop-wise to hexane (1.5 L–3.0 L of residue for 10–15 L of hexane) to yield a precipitate which is filtered and dried under high vacuum (1 mm to 2 mm) at a temperature of 40° C. to yield about 0.5–0.6 kg of a solid residue;
5) the solid residue obtained in the previous step is dissolved in 0,5 L of acetone-methylene chloride to form a 1:9 v/v mixture and subjected chromatography in a silica column; Cephalomannine is co-eluted out with Paclitaxel; the fractions containing Paclitaxel and Cephalomannine are pooled together and rotary evaporated to dryness, the solid residue being a crude mixture of Paclitaxel and Cephalomannine containing from 36 to 40 grams of Paclitaxel (45–55%);
6) a crude mixture (10 g) obtained in the previous step is chemically modified to separate Paclitaxel from Cephalomannine by bromination; the solid residue obtained after bromination reaction having a weight of 13.2 g;
7) the brominated residue is dissolved in acetone/methylene chloride (1:9 v/v) and chromatographically separated over a silica column, the fractions containing Paclitaxel are pooled together and evaporated to dryness; and
8) the solid residue obtained in the previous step is dissolved in acetone and crystallized with an equal volume of n-hexane or other hexanes; and the crystals are washed with cold acetone/hexane, 1/1 v/v solution, filtered, and dried under vacuum at 40° C., the so obtained solid crystals weighing 4.84 g and containing >97% w/w of Paclitaxel as measured by HPLC chromatography.

U.S. Pat. Nos. 5,475,120 and 5,670,673 issued to Rao discloses a process for the isolation of Paclitaxel. In this process:

1) barks, needles, wood, roots, or a combination thereof, are treated with an alcohol and the obtained extract is concentrated under pressure (<35–40° C.) to remove most of the alcohol;
2) the concentrate is partitioned with chloroform (or dichloromethane, dichloroethane or trichloroethane), the chloroform extract is concentrated under reduced pressure to form a thick syrup, and the syrup is poured into glass dishes and dried in a vacuum oven (<40° C.) to form a powder if barks or wood are used, or needle-shaped crystals if needles are used (from 100 kg of the wood or barks, the yield of extract was 1.5–2.5 kg and from 100 kg of needles, it was 2.4–4.8 kg);
3) chloroform solid extracts (2–2.5 kg) are dissolved in acetonitrile (5 L) and water (5 L) was added; the mixture was then equilibrated with silica gel (2–3 L of slurry); more water (15 L) is added gradually while stirring the mixture; the clear solution is siphoned off and the thick slurry of silica gel which is now impregnated with the sample, is transferred onto the top of a stainless steel column; fractions containing Paclitaxel and various important Paclitaxel analogs, are set aside in a hood where slow evaporation of the solvent is carried out; crystals forming after in 1 to 2 days and the process is allowed to continue for 8–10 days; and
4) the so-obtained crude crystals which have less than 5% of Cephalomannine, are crystallized twice with a acetone/ligroin mixture and by using charcoal, thereby yielding 41 g of pure Paclitaxel, viz. a yield of 0.04%, the above yield being obtained with 100 kg of bark; alternatively, the crude crystals are decolorized by passing a solution in chloroform through a short column of silica or Florisil®. Another alternative method for removing the Cephalomannine contaminant consists of using ozone. Washing of the column with a mixture of 1–2% methanol in chloroform gave a bulk of Paclitaxel which can be recovered by concentration and crystallization. The yield is nearly the same as before, 40 g. HPLC chromatography analysis shows that the so recovered Paclitaxel contains less than 0.3% of Cephalomannine.

U.S. Pat. No. 5,969,165 issued to Liu discloses a process for the isolation and purification of Paclitaxel and other related compounds from *Taxus canadensis* by industrial preparative low pressure chromatography.

In this process, needles and twigs of *Taxus canadensis* (200 kg) are extracted with 1000 L of methanol at 60° C. for 5 hours and then filtered. The raw materials are extracted with 700 L of methanol at 55–60° C. for another 4 hours and filtered. The filtrate is combined and mixed with 10 kg of activated carbon (5% w/w). The activated carbon is removed by filtration. The filtrate is then concentrated to approximately 100 L. Then 300 L of water and dichloromethane (1:1) are added. The organic layer is collected and the aqueous solution is extracted two more times with 200 L of dichloromethane. The dichloromethane solution is combined and evaporated to form a slurry and then diluted with 20 L of acetone.

The acetone solution is coated onto 20 kg of Celite® 545 and dried and then loaded onto the top of three industrial low pressure chromatographic columns (150 times. 15 cm). Each column is packed with 15 kg of an aluminium oxide absorbent. The columns are eluted with a solvent system consisting of a mixture of hexane and acetone under a pressure between 10 and 15 psi with a flow rate of about 150 ml/min.

Fractions containing taxanes are collected and combined and then are concentrated to remove all other solvents. The resulting material is dissolved in methanol and kept at room temperature overnight to yield needle-like crystals. The crystals are filtered and recrystallized from acetone to yield white needle-like crystals identified as 13-acetyl-9-dihydrobaccatin III.

The filtrate is concentrated to dryness. The residue is dissolved in 3 L of acetone. The acetone solution is mixed with 1.5 kg of a polystyrene-divinylbenzene. The solvent is removed by evaporation and the resulting powder is loaded on top of an industrial low-pressure chromatographic column packed with polystyrene-divinylbenzene, and is eluted with 45% acetone in water at a flow rate of 150 ml/min under an operating pressure below 30 psi.

Fractions containing Paclitaxel and Cephalomannine are combined and evaporated to remove most of the acetone, then diluted with deionized water and extracted three times with 2,5 L of dichloromethane. The organic layer is concentrated to dryness and the residue is dissolved in 1 L of methanol.

Approximately 30% (v/v) of water is added to the methanol solution and the mixture is warmed to 60° C. for a few minutes, and then kept at room temperature overnight. The crude crystalline solid from the methanol solution is filtered out and dried in a vacuum oven at 70–75° C. The solid consists of approximately 70% Paclitaxel and 25% Cephalomannine in a yield of 31 grams for 200 kg of needles and twigs of *Taxus canadensis*.

The crude Paclitaxel is dissolved in 200 ml of acetonitrile and diluted with 250 ml of deionised water and loaded to a chromatographic column. The chromatographic column is packed with a polymer resin (Diaion®, which is a macroporous polymethacrylate resin). The column is eluted with a step gradient of 35, 40, 45 and 50% acetonitrile in water.

The obtained fractions containing Paclitaxel or Cephalomannine are separately combined and kept at 5° C. until crystallization. Then, Paclitaxel and Cephalomannine crystals are filtered separately and both are recrystallized at 65° C. with a mixture of methanol and water.

Paclitaxel is obtained as white needle-like crystals with a purity >99% at yield of 18.5 g (0.009%). Cephalomannine is obtained with a purity >98% at a yield of 6.5 g (0.003%).

Thus, review of the known processes for the purification of Paclitaxel as disclosed in the prior art known to the Applicant shows that to obtain a high purity Paclitaxel, one must carry out numerous steps of separation by chromatography and purification by crystallization. This leads to a very high production cost due in particular to the low of Paclitaxel in the different species of Taxus. Moreover, the amount of biomass which can be purified, is very limited because of the small sizes of the chromatographic columns and because of the low yield in Paclitaxel obtained after purification.

OBJECTS AND SUMMARY OF THE INVENTION

A first object of the present invention is to provide a process which permits:
- to make easier the obtention of a biomass after extraction of the barks, needles and/or branches of Taxus of different species;
- to increase the amount of biomass which is so obtained and has to be purified by chromatography;
- to reduce the steps of purification;
- to increase the amount of obtained Paclitaxel; and finally
- to reduce the production cost to a more economical level.

Another object of the invention is to provide a mixture of Paclitaxel crystals having a high purity.

In accordance with the present invention, the first object mentioned hereinabove is achieved with process for the extraction and purification of Paclitaxel from a natural source of taxanes containing the Paclitaxel to be extracted, which process comprises the following steps:

a) extracting, with an organic solvent, a raw material comprising Paclitaxel from said natural source of taxanes;

b) treating said raw material with a basic medium or an acidic medium to obtain a biomass by precipitation, isolating said biomass and drying it;

c) removing resin and natural pigments contained in the isolated and dried biomass by dissolving said biomass in acetone and then adding thereto at least one non-polar solvent until a Paclitaxel-enriched oily phase is obtained;

d) treating the biomass contained in the Paclitaxel-enriched oily phase recovered in the preceding step with an acidic medium when step (b) was carried out with a basic medium, or with a basic medium when step (b) was carried out with an acidic medium to obtain another biomass by precipitation, isolating said precipitate and drying it;

e) chromatographically purifying at least once a solution of the isolated other biomass obtained in the preceding step in a volatile solvent, and crystallizing at least once the purified solution obtained by chromatography.

In accordance with the invention, the second object mentioned hereinabove is achieved by a mixture of Paclitaxel crystals, which is obtained by the above process and which, after filtration and drying of the crystals consists of:
- about 53% of crystals having a purity higher than 99%,
- about 22% of crystals having a purity higher than 98%, and
- about 23% of crystals having a purity higher than 92%.

The present invention, its advantages and the way it can be reduced to practice will be better understood upon reading the following non-restrictive description.

DETAILED DESCRIPTION OF THE INVENTION

Figure 1A:
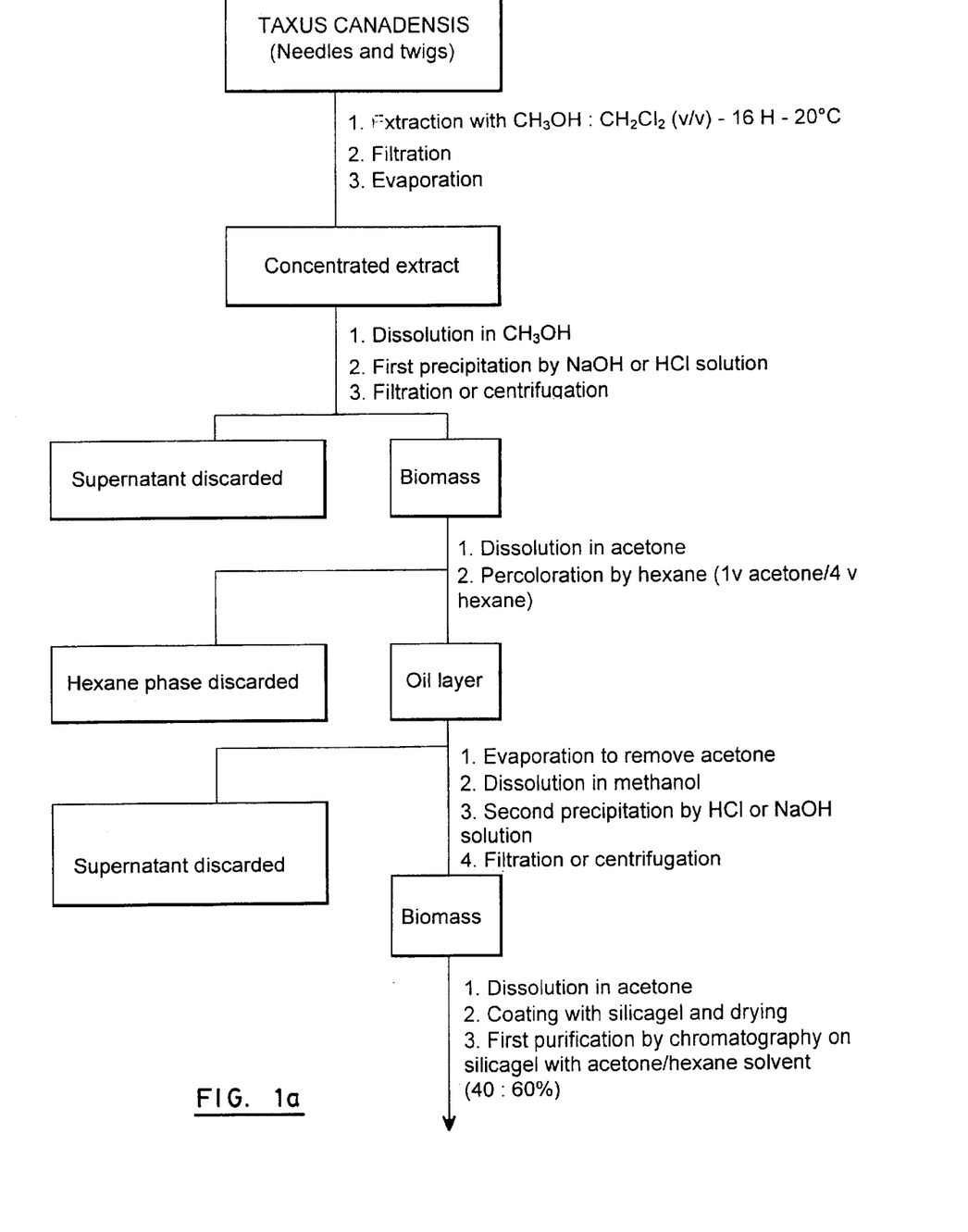
FIGS. 1a, 1b and 1c are a flow chart illustrating the process according to the invention.
Figure 1B:
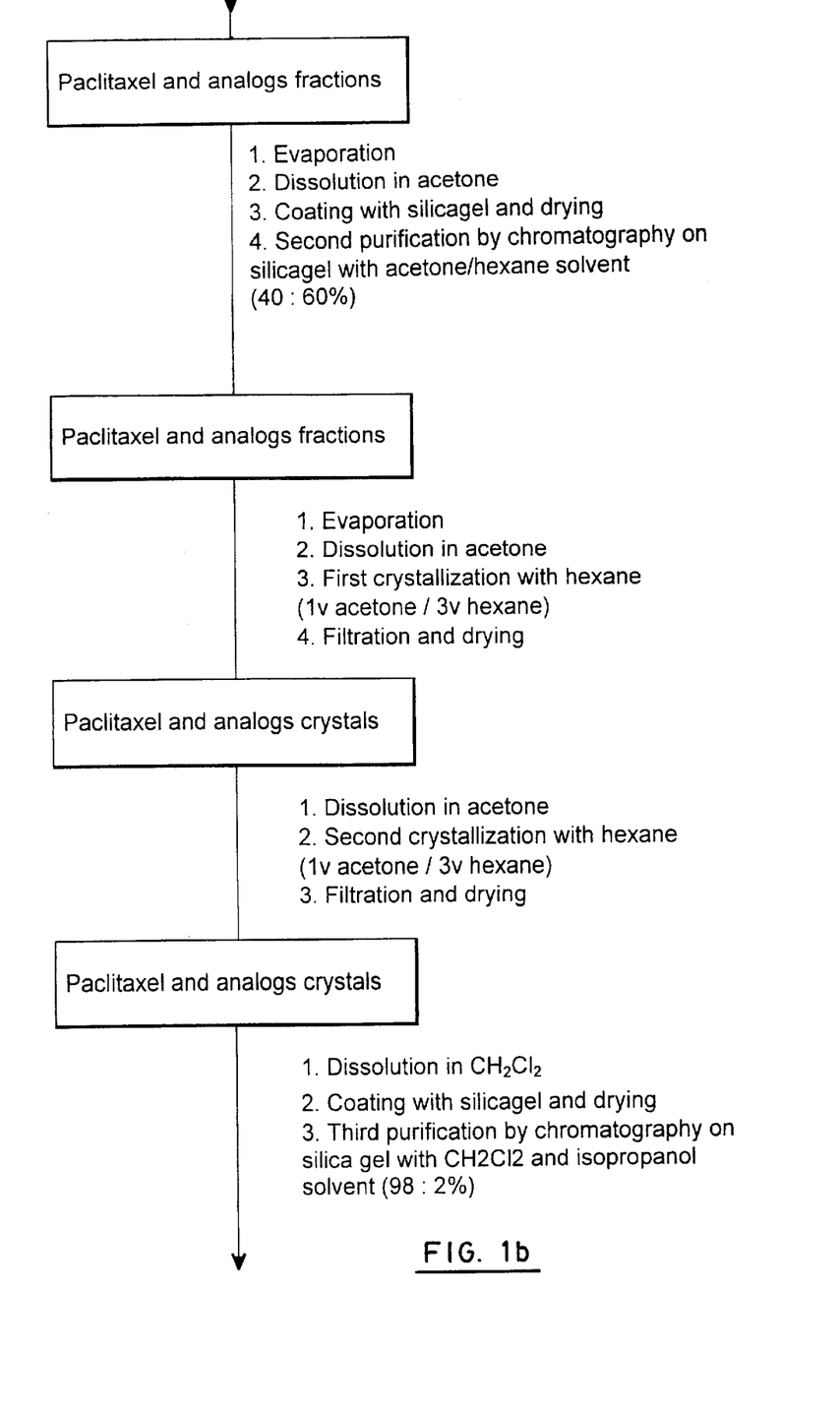
Figure 1C:
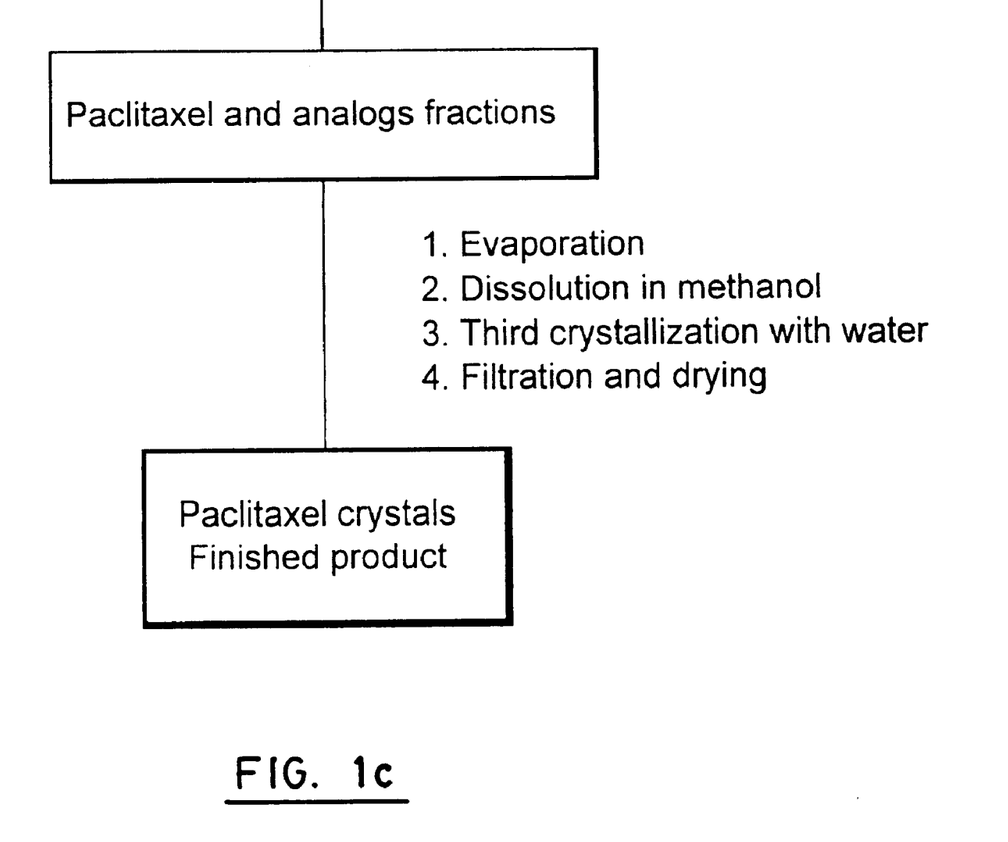

Within the scope of the present invention and in the following description, the expression "to percolorize" means "to remove resin and pigments from a solution by adding a non polar solvent which may be miscible or unmiscible with the solution".

As aforesaid, the process according to the invention is intended to be used for the extraction and purification of Paclitaxel from a natural source of taxanes containing the Paclitaxel to be extracted.

Step 1—Extraction

The first step of the process consists of extracting a raw material containing Paclitaxel and its analogs from a natural source of taxanes, using an organic solvent mixture to do so.

The natural source of taxanes used as starting material for carrying out the process according to the invention is of Taxus type. More particularly, it consists of any one of the species of conifers that contain Paclitaxel. Such species of conifer containing Paclitaxel may consist of *Taxus brevifolia, Taxus baccata, Taxus canadensis, Taxus wallichiana, Taxus yunnanensis, Taxus densiformis, Taxus hicksii, Taxus wardii, Taxus cuspidata, Taxus capitata* or *Taxus brownii*.

The process according to the invention has the advantage of being usable with any part of the natural source of taxanes which contains Paclitaxel. Preferably, the extraction is carried out from barks of the selected conifer(s). Alternatively, the extraction can be carried out by simultaneously using branches and needles of the selected conifers.

Preferably, the extract that is so obtained is filtered to remove deposits, and is decanted in a double wall tank in which hot water (preferably at a temperature of 65–70° C.) is fed. The solvent is distilled from this tank until a very thick liquid is obtained. The extract is then recovered and dissolved in methanol.

In the extraction step, the organic solvent that is used, is preferably selected from the group consisting of alcohols, halogenated hydrocarbons and mixtures of alcohols and halogenated hydrocarbons. As examples of such solvents, reference can be made to methanol, dichloromethane, trichloromethane and mixtures of methanol with dichloromethane or trichloromethane.

In the case where one uses a mixture of halogenated hydrocarbon and alcohol, the alcohol and halogenated hydrocarbon are present in volume ratio preferably comprised between 9:1 and 1:9. More preferably, the volume ratio of the mixture is equal to about 1:1.

2—First Precipitation

The second step of the process consists of treating the raw material either in a basic medium or an acidic medium to obtain precipitation of a biomass.

In the case where the precipitation is carried out in a basic medium, this medium preferably consists of a solution of a basic salt such as sodium acetate, potassium acetate or tris(hydroximethyl)aminomethane (also called TRIS).

According to a preferred embodiment, the basic medium consists of a solution of sodium hydroxide and the sodium hydroxide is used in a concentration ranging between 10 millimoles and 80 millimoles per liter of solution and more preferably between 20 millimoles and 50 millimoles per liter of solution.

The pH of the basic medium is usually comprised between 8.5 and 11, preferably between 9 and 10.

When the precipitation is carried out in an acidic medium, the acidic medium usually consists of a mineral acid solution or an organic acid solution. The acid can be selected from the group consisting of chlorhydric, acetic and citric acids.

The concentration of acid in the solution is preferably comprised between 10 millimoles and 50 millimoles per liter of solution, and more preferably between 20 millimoles and 30 millimoles per liter of solution.

The pH of the acidic medium is preferably comprised between 2 and 4.

In all cases, the volume of the basic or acidic solution added to the raw material to achieve precipitation of the biomass is equal to 1 to 20 times the volume of the raw material extracted in the first step of the process.

When use is made of a basic solution, the volume of basic solution added to the raw material is preferably equal to 1 to 15 times the volume of the raw material. When use is made of an acidic solution, the volume of acidic solution added to the raw material is preferably equal to 1 to 10 times the volume of raw material obtained in the first step of the process.

Under these conditions, the precipitate that is formed is very fine and light and its filtration is very difficult. As a matter of fact, the precipitate cannot be totally recovered by centrifugation at low speed (5,000 rpm). A speed of 15,000 or even 20,000 rpm is necessary to efficiently separate the precipitate from the solution.

To solve this problem and facilitate isolation of the precipitate from the so obtained biomass, the biomass may be salted before isolation and drying by addition of sodium chloride in a concentration comprised between 25 and 200 grams per liter of the acidic or basic solution used for the precipitation. Preferably, sodium chloride is added in a concentration comprised between 50 and 100, and more preferably between 50 and 75 grams per liter of acidic or basic solution used for the precipitation.

Salting the solution with sodium chloride permits to obtain a flocculation. The obtained precipitate is then heavier, more agglomerated and easier to filter or centrifuge at low speed.

Sodium chloride is preferably added quickly to the solution under heavy stirring.

According to another preferred embodiment of the invention, the biomass precipitated in this step is separated from the solution by filtration or by centrifugation and then dried at ambient air or under vacuum, preferably by ventilation or lyophilization.

Step 3—Percolorization

The third step of the process according to the invention consists of percolorizing the biomass isolated in the preceding step.

More specifically, in this third step, the biomass obtained from the preceding step of precipitation is put back in solution by adding thereto a volume of acetone equal to about 2 volumes of the raw material extracted in step 1, before precipitation.

More preferably, the biomass is put back in solution by first adding acetone and then by adding water. Water is preferably added at a ratio of 2 to 10 volumes, and more preferably 5 to 7 volumes, per 100 volumes of added acetone.

After such a dissolution, at least one non-polar solvent is added to the obtained solution to form a Paclitaxel-enriched oily phase.

The non-polar solvent(s) used in this percolorization step is (are) preferably selected from the group consisting of hydrocarbons miscible with acetone, such as hexane or heptane. When use is made of hexane, the volume of hexane that is used is usually 3 to 4 times that of the acetone solution.

The mixture that is obtained is then transferred into a decanting flask and the oily phase containing Paclitaxel and the other taxanes that are deposited at the bottom of the flask, are recovered. The oily phase is then evaporated and replaced by methanol.

This third step permits to eliminate most of the resin and natural pigments of the conifers used as starting material.

Step 4—Second Precipitation

The fourth step of the process according to the invention consists of treating with a base or an acid the biomass contained in the Paclitaxel-enriched oily phase recovered in the preceding step to obtain another biomass by precipitation, used then isolating this other biomass and drying it.

More specifically, in this fourth step, the Paclitaxel-enriched phase obtained in the preceding step is first evaporated to dryness and put back in solution with methanol.

The so-obtained methanol solution is then precipitated in a basic medium when the first precipitation step hereinabove called step 2 has been carried in an acidic medium, or in a basic medium when the first precipitation step has been carried out in an acidic medium. The purpose of this precipitation is to obtain a biomass containing Paclitaxel in the form of a precipitate.

According to a preferred embodiment of the invention, the biomass that is so-obtained by precipitation, is further salted before isolation and drying, by adding thereto sodium chloride at a concentration comprised between 30 and 200 grams per liter of the acidic or basic solution used for the precipitation. Preferably, sodium chloride is added at a concentration comprised between 50 and 100 grams per liter of the acidic or basic solution used for the precipitation.

The precipitate contained in the biomass is then filtered and dried at ambient air or under vacuum, or is lyophilized.

The precipitate formed in this step is very fine and light, thereby making its filtration very difficult. As a matter of act, this precipitate can only be recovered partially if the centrifugation is carried out at a low speed (for example 5,000 rpm). Only a speed of 15,000 and 20,000 rpm would allow full separation of the precipitate from its solution. Thus, it is once again suitable to add sodium chloride to the solution to obtain a flocculation which makes the precipitate heavier, more agglomerated and easier to filter or centrifuge at low speed. The concentration of sodium chloride used for this treatment is preferably from 25 to 100 g per liter of solution, and more preferably from 50 to 75 g per liter of solution. Sodium chloride is added quickly into the solution under heavy stirring.

Step 5—Chromatographic Purification

The fifth and last step of the process according to the invention consists of chromatographically purifying at least once a solution of the isolated other biomass obtained in the preceding step in a volatile solvent, and crystallizing at least once the purified solution obtained by chromatography.

To do so, the precipitate obtained after drying in step 4 is dissolved in a volatile solvent and then submitted to at least one step of chromatographic purification and at least one step of crystallization of the purified solution obtained by chromatography. Preferably however, the precipitate obtained after drying in step 4 is submitted to several chromatographic purifications and several crystallizations, the number of successive purifications and crystallizations being preferably equal to three.

These three successive purifications and crystallizations will now be described as sub-steps A to F.

A—First Chromatographic Purification

In the first chromatographic purification step, the biomass obtained in step 4 of the process is dissolved in a volatile solvent. The obtained solution is mixed with silica gel and dried under ventilation, and then the silica gel covered with the biomass is loaded onto a chromatographic column containing the same type of gel. In this column, the biomass is purified with an elution mixture comprising from 30 to 40% acetone and from 60 to 70% hexane. Preferably, the elution mixture comprises about 40% acetone and about 60% hexane.

The volatile solvent used for the dissolution is preferably acetone. The acetone solution is then filtered to remove the insoluble particles and mixed with silica gel. The so obtained mixture is then dried under ventilation or under vacuum.

The gel impregnated with Paclitaxel and its analogs is loaded onto the column which preferably has a height of 142 cm and an inside diameter of 76 cm and which contains 2.2–2.3 kg silica gel. The gel of the column is washed and balanced with the elution mixture consisting of acetone and hexane (40–60%, volume per volume). Elution of the fractions is carried out with the same solvent mixture at a flow rate of about 100 ml/min, under a pressure varying from 0 to 30 psi.

B—Second Chromatographic Purification

In the second chromatographic purification step, the Paclitaxel-enriched fractions recovered in the preceding step are preferably combined and then evaporated to dryness until a residue is obtained.

A solution of the residue is then prepared by solubilisation in a volatile solvent. The so obtained solution is then repurified by chromatography under the same conditions as in the preceding step to provide new Paclitaxel-enriched fractions.

According to a preferred embodiment, the residue is dissolved in acetone, and then mixed with silica gel and dried.

The gel impregnated with Paclitaxel and its analogs is loaded onto a column (142 cm long×7.6 cm inside diameter) containing 2.2–2.3 kg silica gel. The gel of the column is washed and balanced with an elution mixture consisting of acetone and hexane (40–60%, volume per volume). Elution of the fractions is carried out with the same solvent mixture at a flow rate of about 100 ml/min, under a pressure of between 0–30 psi.

The fractions containing the Paclitaxel (in general from 40 to 60% Paclitaxel) are once again combined.

C—First Crystallization

In this step, the fractions containing Paclitaxel obtained by chromatography in the preceding purification step, are evaporated to dryness and put back in solution in acetone. The amount of acetone is adjusted to obtain an absorbency of solution having a value from 1.0 to 1.5 O.D. for the peak corresponding to Paclitaxel according to HPLC analysis. Then, the Paclitaxel is crystallized by adding from 3 to 4 volumes of hexane in the acetone solution.

Crystals are formed rapidly. The mixture is left to rest overnight at ambient temperature or at a temperature comprised between 2 and 8° C. to complete the crystallization.

D—Second Crystallization

In this step, the crystals obtained by recrystallization in the preceding step are separated by filtration and put back in solution in acetone with a volume of acetone adjusted to obtain an absorbency of the solution varying from 1.0 to 1.5 O.D. for the peak corresponding to Paclitaxel according to HPLC analysis.

The Paclitaxel contained in this solution is then recrystallized by adding to the acetone solution 3 to 4 volumes of hexane per volume of solution.

The crystals obtained in this step have, according to HPLC analysis, a Paclitaxel purity higher than 80%.

E—Third Chromatographic Purification

In this step, the crystals obtained in the preceding step are filtered and then put back in solution with methylene chloride.

The so obtained solution is then mixed with silica gel and dried under ventilation.

The silica gel coated with Paclitaxel is loaded onto a chromatographic column containing the same type of gel. The Paclitaxel is then repurified for the third time with an organic-solvent based elution mixture. Preferably, the elution mixture comprises from 95 to 98% methylene chloride and from 2 to 5% isopropanol.

Preferably, in this step, the crystals are dissolved with methylene chloride, mixed with silica gel and dried. The gel impregnated with Paclitaxel is loaded onto a chromatographic column (76 cm long×7.6 cm inside diameter) containing 1.5–1.6 kg of silica gel. The gel of the column is washed and balanced with a solvent consisting of methylene chloride and isopropanol (98-2% per volume). Elution of the fractions is carried out with the same mixture of solvents, at a flow rate is about 50 ml/min under the pressure ranging between 0–30 psi.

F—Third Crystallization

In this step, the enriched fractions containing Paclitaxel recovered by chromatography in the preceding step are combined according to their purity, preferably according to purities of +98 to +99 and 90 to 98%. Then, they are evaporated to dryness and put back in solution in an alcohol, preferably methanol, a ketone or an alcohol-ketone mixture.

The volume of added solvent, preferably methanol, is adjusted to obtain an absorbency varying from 1.0 to 1.5 O.D. for the peak corresponding to Paclitaxel according to HPLC analysis.

The Paclitaxel is then recrystallized for a third time by adding to the methanol solution from 2 to 10 volumes of water per volume of solution. Preferably, use is made of 4 to 7 volumes of water per volume of methanol solution.

In the last step of purification and of recrystallization disclosed hereinabove, the water that is used is preferably is a purified water obtained by deionization and/or distillation.

According to a preferred embodiment, 7 to 10 volumes of pure water cooled to a temperature of 2 to 4° C. are added to a volume of the methanol solution cooled in ice. Then, the crystals appear immediately. Crystallization is continued all night at a temperature comprised between 2–4° C.

Addition of water in the methanol solution can be done at ambient temperature. The formation of the crystals will then be slower but it will be completed overnight at 2–4° C. The crystals are filtered and dried under ventilation or under vacuum, in order to obtain a fine and detached powder. The crystals are then put back in suspension in pure water and lyophilized during 66 to 72 hours at a temperature of about −60° C.

The obtained fractions of taxanes can be analysed by HPLC chromatography (Waters system) using an Autosampler (Waters 717 plus), a Photodiode Array Detector (Waters 996), a Multisolvent Delivery System (Waters® 600E) and a C18 Nova-Pak® column, 60 Å, 4 μm (3.9×150 mm).

Analysis of the fractions is carried out by injecting a volume of 5 μl. The flow rate of the mobile phase is about 1 ml/min, when using a solvent gradient: acetonitrile-water-methanol (20:50:30 at the beginning; 35:35:30 at the end).

The peaks of the compounds are detected at 228 nm and the time of analysis of a sample is about 36 minutes.

Preferably, the volatile solvent used in the chromatographic purification step for the solubilization of the residue is selected from the group consisting of cetones, C1–C3 light alcohols, ethyl acetate, methylene chloride and mixtures of these solvents.

At the end of step F, after crystallization of the Paclitaxel in water and after filtering and drying, a mixture of Paclitaxel crystals is obtained. This mixture of Paclitaxel crystals consists of:

53% of crystals having a purity higher than 99%;

22% of crystals having a purity higher than 98%; and

23% of crystals having a purity higher than 92%.

The following examples are given for the sole purpose of illustration and should not be considered as to limit the scope of the present invention.

EXAMPLE 1

Extraction 50 kg of dried needles and twigs of *Taxus canadensis* were washed with deionised water and dried under ventilation. The raw materials were ground and transferred into a cotton bag. This bag was put into a stainless steel tank containing 150 L of a solvent mixture (methylene chloride—methanol; 1:1 volume per volume). The extraction was carried out during 16 hours at ambient temperature. The extract was pumped through filters into a second double wall tank. The solvent was distilled with the aid of hot water at 70° C. circulating in the double wall of the tank until a very thick liquid was obtained.

First Precipitation

The extract concentrate was recovered and diluted with 2 L of methanol. The biomass was isolated by precipitation by adding the extract to a NaOH solution at 20 mM. A very fine precipitate was formed as the extract was added to the NaOH solution. The volume ratio of the extract to the basic solution was about 1:15.

This fine precipitate was very difficult to filter. Only a centrifugation at very high speed (15,000–20,000 rpm) could allow recovery of the biomass. Thus, NaCl was added to the solution at a ratio of 50 g/L of solution in order to make the precipitate more agglomerated. The precipitate was then filtered or centrifuged at a speed of only 4200 rpm at 20° C. during 30 minutes (J6MC Beckman® Centrifugal machine, 4.2 JS rotor). It may be understood that a continuous flow centrifugal machine can be used to process large amounts of precipitate.

The so obtained precipitate was air or vacuum dried or was lyophilized (Freeze dryer—FTS Systems). The weight of the precipitate was about 500–550 g. This precipitate was solubilised in 2 L of acetone and filtered or centrifuged at 4200 rpm, at 0–2° C. during 30 minutes, in order to remove the insoluble particles contained therein.

Percolorization

Then, 1 L of the acetone solution was fed into a flask of 6 L, the solution was mixed with 4 L of hexane by successive addition of 1 L of hexane each followed by a heavy manual shaking. The mixture was allowed to rest for about 10 minutes, and the oily phase was recovered at the bottom of the flask.

In practice, the acetone solution can be treated in one batch by using a large Becher or an adequate tank from which the hexane phase can be siphoned off and the remaining liquid be transferred into a separating flask to complete recovery of the oily phase.

During this step, the highly coloured hexane phase was discarded.

Second Precipitation

The oily phase was then evaporated to dryness. The residue was dissolved in 2 L of methanol. The biomass was isolated for the second time by precipitation achieved by adding the methanol solution in a solution of HCl at 20 mM. A very fine precipitate was formed as the extract was added. The volume ratio of the extract to the acidic solution was about 1:5. Once again, this fine precipitate was very difficult to filter. Only a centrifugation at high speed (15,000–20,000 rpm) could allow recovery of the biomass. Thus, NaCl was again added to the solution (50 g/L of solution) to make the precipitate more agglomerated. The precipitate was then filtered or centrifuged at a speed of 4200 rpm only, at 20° C. during 30 minutes (J6MC Beckman® Centrifugal machine, 4.2 JS rotor). Once again, a continuous flow centrifugal machine can be used to process large amounts of precipitate.

First Purification by Chromatography on Silica Gel at Low Pressure

The recovered precipitate was dried with air or under vacuum or lyophilized. The weight of the precipitate was about 240–260 g. This precipitate was solubilised in 0.5 L of acetone and centrifuged at 4200 rpm, at 0–2° C., during 30 minutes to remove the insoluble particles contained therein. The acetone solution was then mixed with 200–250 g of silica gel (230–400 mesh, pharmaceutical quality, Silicycle®, Quebec, Canada). The gel impregnated with the extract was air dried under ventilation or under vacuum. The dried gel was loaded onto a column (142×7.6 cm inside diameter) containing 2.2 kg of silica gel (230–400 mesh). The gel was washed and balanced with a mixture of acetone and hexane (40:60%, volume per volume). The elution was carried out with the same solvent, using a Dynamax® solvent delivery system. The flow rate of the elution was about 100 ml/min under a pressure between 10–30 psi. The volume of solvent mixture was about 30 L and each fraction was collected in batches using with 1 L of solvent purification. HPLC analysis indicated that from the $17^{th}$ to $25^{th}$ fractions obtained, there were 9 fractions which contained Paclitaxel.

The Paclitaxel contents in these fractions as determined by HPLC were respectively as follows: 11; 24; 32; 40; 38; 33; 29; 14 and 9%.

It is worth noting that the fractions containing Paclitaxel can be offset with respect to the others from one purification to the other.

Second Purification by Chromatography on Silica Gel at Low Pressure

The fractions containing Paclitaxel were combined together and evaporated to dryness. The residue was resolubilised in 100 ml of acetone and put into contact with 100 g of silica gel. The gel coated with Paclitaxel was air dried under ventilation or under vacuum. The dried gel was loaded into a column (142×7.6 cm inside diameter) containing 2.2 kg of silica gel (230–400 mesh). The gel was washed and balanced with a mixture of acetone and hexane (40:60%, volume per volume). The elution was carried out with the same solvent using a solvent delivery system. The flow rate of the elution was about 100 ml/min under a pressure between 10–30 psi. The volume of solvent mixture was about 30 L and the fractions were collected in batches of using 1 L of solvent per fraction. HPLC analysis indicated that there were 5 fractions which contained Paclitaxel, from the $22^{nd}$ fraction to the $26^{th}$ fractions. The Paclitaxel content determined by HPLC in these fractions were as follows: 40; 58; 66; 50 and 49%. Once again, these fractions containing Paclitaxel can be offset with respect to the others from one purification step to the other.

First Crystallization

The fractions containing Paclitaxel were combined and evaporated to dryness. The residue was resolubilised in 800 ml of acetone. Adjustment of acetone volume was necessary on HPLC analysis so as to obtain an absorbency from 1.0 to 1.5 O.D. for the Paclitaxel peaks. 3 volumes of hexane (2.4 L) were added to the acetone solution. Crystals were formed in the following hour. The mixture was kept at a temperature comprised between 2–8° C. overnight to complete the crystallization.

Second Crystallization

The obtained crystals were filtered and redissolved in 400 ml of acetone. 3 volumes of hexane (1.2 L) were added to the acetone solution. Crystals are formed in the following hour. The mixture was kept at a temperature comprised between 2–8° C. overnight to complete the crystallization. The crystals were dried with air or under vacuum.

The dried weight of obtained crystals was about 10 g ±0.2 g. HPLC analysis indicated that the Paclitaxel content was of about 80% and higher.

Third Purification by Chromatography on Silica Gel at Low Pressure

The crystals were once again dissolved in 75 ml of methylene chloride and put into contact with 75 g of silica gel. The gel coated with Paclitaxel was air dried under ventilation or under vacuum. The dried gel was loaded onto a column (76×7.6 cm inside diameter) containing 1.5 kg of silica gel (230–400 mesh). The gel was washed and balanced with a mixture of methylene chloride and isopropanol (98:2%, volume per volume). The elution was carried out with the same solvent using a Dynamax® solvent delivery system. The flow rate of the elution was about 50 ml/min under a pressure between 10–30 psi. The volume of solvent mixture was about 30 L and the fractions were collected with 1 L of solvent per fraction. HPLC analysis indicates that there are 12 fractions which contain Paclitaxel, from the $11^{th}$ fraction to the $22^{nd}$ fractions. The Paclitaxel contents determined by HPLC in these fractions, were as follows: 80; 97; 99.50; 99.70; 99.70; 99.30; 98.60; 97.30; 94; 92; 89 and 85%. Once again, the fractions containing Paclitaxel can be offset with respect to the others from one purification step to the other.

Third Crystallization

The fractions containing Paclitaxel were combined to their respective purities and evaporated to dryness. The $12^{th}$ to $16^{th}$ fractions were dissolved in 100 ml of methanol (HPLC grade), $17^{th}$ to $18^{th}$ fractions were dissolved in 45 ml of methanol (HPLC grade) and the $19^{th}$ to $22^{th}$ fractions were dissolved in 75 ml of methanol (HPLC grade).

1) 700 ml of water (HPLC grade) cooled beforehand at 2–8° C. were added to the methanol solution ($12^{th}$ to $16^{th}$ fractions) cooled in ice. White crystals appeared immediately
2) 300 ml of water (HPLC grade) cooled beforehand at 2–8° C. were added to the methanol solution ($17^{th}$ and $18^{th}$ fractions) cooled in ice. White crystals appeared immediately.
3) 500 ml of water (HPLC grade) cooled beforehand at 2–8° C. were added to the methanol solution ($19^{th}$ to $22^{th}$ fractions) cooled in ice. White crystals appeared immediately.

The crystals were separately filtered and dried with air or under vacuum. The dried weights and the purities of the crystals analysed by HPLC were as follows:

$12^{th}$ to $16^{th}$ fractions: 3.40 g—Purity: 99.30%
$17^{th}$ to $18^{th}$ fractions: 1.40 g—Purity: 98.85%
$19^{th}$ to $22^{th}$ fractions: 1.60 g—Purity: 92.70%

Crystals which had a purity inferior to 98% were set aside and repurified together by chromatography under the same conditions as in the $3^{rd}$ purification step described above. This repurification allowed to obtain about 75% of the total amount of crystals with a purity higher than to 99%.

EXAMPLE 2

The process disclosed in example 2 was similar to the one disclosed in example 1 except for the first and second precipitation steps that were carried as follows.

First Precipitation

The extract concentrate was recovered and diluted with 2 L of methanol. The biomass was isolated by precipitation by adding the extract to a solution of HCl at 20 mM. A very fine precipitate was formed as the extract was added. The volume of ratio of the extract with respect to the acidic solution was about 1:10. The fine precipitate was very difficult to filter. Only a centrifugation at high speed: (15,000–20,000 rpm) could allow recovery of the biomass. Thus, NaCl was added to the solution at a ratio of 50 g/L of solution in order to make the precipitate more agglomerated. The precipitate was centrifuged at 4200 rpm at 20° C. during 30 minutes (J6MC Beckman® Centrifugal machine, 4.2 JS rotor).

The recovered precipitate was dried with air or under vacuum or lyophilized. The weight of the precipitate was about 500–520 g. This precipitate was solubilised in 2 L of acetone and filtered or centrifuged at 4200 rpm at 0–2° C. during 30 minutes, to remove the insoluble particles contained therein.

Second Precipitation

The oily phase was then evaporated to dryness. The residue was dissolved in 2 L of methanol. The biomass was isolated for a second time by precipitation by adding the methanol solution to a solution of NaOH at 20 mM. A very fine precipitate was formed as the extract was added. The volume ratio of the extract with respect to the basic solution was about 1:5. This fine precipitate was very difficult to filter. Only a centrifugation at high speed (15,000–20,000 rpm) would have permit to recuperate the biomass. Therefore, NaCl was added to the solution in a ratio of 50 g/L of solution, in order to make the precipitate more agglomerated. The precipitate was then filtered and centrifuged at 4200 rpm at 20° C. during 30 minutes (J6MC Beckman®, 4.2 JS rotor).

The yield and the purities of the Paclitaxel obtained in this example 2 were identical to those obtained in example 1.

The above examples show that the process according to the invention provides a substantial decrease in the production cost of Paclitaxel as compared to the different processes known in the art. This cost decrease is caused by an increase of the Paclitaxel yield with acceptable therapeutic purity and by noticeable savings in terms of non-recoverable products (solvents, gel . . . ) and production time. In addition to these advantages, the present invention provides a very simple, fast and easy process that can be used at an industrial level without being limited by the low amount of Paclitaxel contained in the treated biomasses.

What is claimed is:

1. A process for extraction and purification of Paclitaxel from a natural source of taxanes, said process comprising the steps of:
   a) extracting a raw material comprising Paclitaxel from said natural source of taxanes with an organic solvent;
   b) contacting said raw material with a basic medium or an acidic medium to obtain a biomass by precipitation, isolating and drying said biomass;
   c) removing resin and natural pigments from the isolated and dried biomass by dissolving said biomass in acetone and then adding thereto at least one non-polar solvent until a Paclitaxel-enriched oily phase is obtained;
   d) contacting the Paclitaxel-enriched oily phase recovered in the preceding step with an acidic medium when step (b) was carried out with the basic medium, or with a basic medium when step (b) was carried out with the acidic medium, in order to obtain a precipitate by precipitation, isolating said precipitate and drying it;
   e) chromatographically purifying at least once a solution of the isolated precipitate in a volatile solvent, and crystallizing at least once the purified solution obtained by chromatography.

2. The process according to claim 1, wherein step e) comprises the following sub-steps:
   $e_1$) dissolving the precipitate isolated in step (d) in a volatile solvent, preparing a mixture of said solution with silica gel, treating said mixture in a chromatographic column comprising silica gel, and recovering first Paclitaxel-enriched fractions;
   $e_2$) evaporating to dryness the first Paclitaxel-enriched fractions until a residue is obtained, and preparing a mixture by solubilizing said residue in a volatile solvent, with silica gel, treating said mixture in a chromatographic column comprising silica gel, and recovering second Paclitaxel-enriched fractions;
   $e_3$) evaporating to dryness the second Paclitaxel-enriched fractions until a residue is obtained, preparing a mixture of said residue in acetone and crystallizing the Paclitaxel contained in the mixture with a non-polar solvent;
   $e_4$) solubilizing in acetone Paclitaxel crystals obtained in sub-step ($e_3$) and recrystallizing the Paclitaxel with a non-polar solvent;
   $e_5$) solubilizing the crystals obtained in sub-step ($e_4$) in a volatile solvent to obtain a solution, preparing a mixture of said solution with silica gel and treating said mixture in a chromatographic column comprising silica gel to obtain, with an elution solvent, third Paclitaxel-enriched fractions; and
   $e_6$) evaporating to dryness the third Paclitaxel-enriched fractions obtained in sub-step ($e_5$) until a residue is obtained, solubilizing the residue in an alcohol, ketone or an alcohol-ketone mixture to obtain a second mixture, and crystallizing the Paclitaxel contained in the second mixture with water.

3. The process according to claim 2, wherein the natural source of taxanes containing Paclitaxel consists of conifers selected from the group consisting of *Taxus brevifolia, Taxus baccata, Taxus canadensis, Taxus wallichiana, Taxus yunnanensis, Taxus densiformis, Taxus hicksii, Taxus wardii, Taxus cuspidata, Taxus capitata* and *Taxus brownii*.

4. The process according to claim 3, wherein, in step (a):
   the raw material is selected from the group consisting of barks, branches and needles of said conifers, or mixtures thereof; and
   the organic solvent is selected from the group consisting of alcohols, halogenated hydrocarbons and mixtures of alcohol and halogenated hydrocarbons.

5. The process according to claim 4, wherein the organic solvent used in step (a) is a mixture of methanol and dichloromethane or trichloromethane.

6. The process according to claim 5, wherein the methanol and dichloromethane or trichloromethane are present in a volume ratio ranging from 9:1 to 1:9.

7. The process according to claim 3, wherein, in step (b), the biomass is precipitated in a basic medium consisting of a solution of a basic salt selected from the group consisting of sodium acetate, potassium acetate, sodium hydroxide and tris(hydroxymethyl)aminomethane.

8. The process according to claim 7, wherein:
   the basic salt is sodium hydroxide;
   the sodium hydroxide is used in a concentration between 10 mM and 80 mM per liter of solution; and
   the pH of the solution is between 8.5 and 11.

9. The process according to claim 3, wherein, in step (b):
   the biomass is precipitated in an acidic medium consisting of a solution of an acid selected from the group consisting of hydrochloric, acetic and citric acids;
   the acid is used in a concentration between 10 mM and 50 mM per liter of solution; and
   the pH of the solution is between 2 and 4.

10. The process according to claim 3, wherein, in step (b), the precipitation of the biomass is made with a solution of said basic medium or acidic medium in a volume ratio of said solution to the raw material extracted in step (a) of between 1 and 10.

11. The process according to claim 10, wherein, in step (b), the precipitated biomass is salted before isolation and drying, by adding thereto sodium chloride in a concentration of between 25 and 200 g per liter of the solution used for the precipitation.

12. The process according to claim 10, wherein, in step (b), the precipitated biomass is separated by filtration or centrifugation, and then dried in air or by lyophilization.

13. The process according to claim 3, wherein in step (c):
the dried biomass obtained in step (b) is dissolved by adding acetone and then water, the water being added thereto at a ratio of 2 to 10 volumes per 100 volumes of acetone added; and said at least one non-polar solvent used in step (c) is selected from the group consisting of hexane and heptane.

14. The process according to claim 3, wherein prior to carrying out step (d):
the Paclitaxel-enriched oily phase obtained in step (c) is evaporated to dryness and dissolved in methanol.

15. The process according to claim 14, wherein the second biomass is salted before isolation and drying by adding thereto sodium chloride at a concentration of between 30 and 200 g per liter of the solution used for the precipitation.

16. The process according to claim 3, wherein:
in step ($e_1$):
the precipitate obtained in step (d) is dissolved in a volatile solvent to form a solution;
the solution is mixed with silica gel and dried in air;
the silica gel is recovered and loaded into a chromatographic column also containing silica gel; and
the precipitate is then purified with an elution mixture containing from 30% to 40% acetone and from 60% to 70% hexane;

in step ($e_2$):
the enriched fractions containing Paclitaxel obtained by chromatography in step (e), are separated, evaporated to dryness and dissolved in a volatile solvent to form a solution;
the solution is mixed with silica gel and dried under ventilation;
the silica gel is recovered and loaded into a chromatographic column also containing silica gel; and
then the Paclitaxel is repurified by an organic solvent mixture comprising from 30% to 40% acetone and from 60% to 70% hexane;

in step ($e_3$):
the fractions containing Paclitaxel obtained by chromatography in step ($e_2$), are separated, evaporated to dryness and dissolved in the acetone to form a solution, the amount of acetone being adjusted so as to obtain an absorbency of said solution having a value of 1.0 to 1.5 O.D. for the peak corresponding to the Paclitaxel according to HPLC analysis; and
the Paclitaxel is then crystallized by adding from 3 to 4 volumes of hexane in the solution;

in step ($e_4$):
the crystals obtained in step ($e_3$) are separated by filtration and dissolved in acetone to form a solution, the volume of acetone being adjusted so as to obtain an absorbency of said solution of from 1.0 to 1.5 O.D. for the peak corresponding to the Paclitaxel according to HPLC analysis; and
the Paclitaxel is then recrystallized by adding from 3 to 4 volumes of hexane in the solution;

in step ($e_5$):
the crystals obtained in step ($e_4$) are filtered and dissolved in methylene chloride to form a solution;
the solution is then mixed with silica gel and dried under ventilation;
the silica gel covered with Paclitaxel is loaded into a chromatographic column also containing silica gel; and
the Paclitaxel is then repurified with an organic-solvent based elution mixture comprising from 95% to 98% methylene chloride and from 2% to 5% isopropanol; and in step ($e_6$):
the enriched fractions containing Paclitaxel obtained by chromatography in step ($e_5$) are separated according to their purity, evaporated to dryness and then dissolved in methanol, the volume of methanol being adjusted so as to obtain an absorbency of from 1.0 to 1.5 O.D. for the peak corresponding to the Paclitaxel according to HPLC analysis; and
the Paclitaxel is then recrystallized by adding from 2 to 10 volumes of water in the methanol solution.

17. The process according to claim 16, wherein the volatile solvent used in steps ($e_1$), ($e_2$) and ($e_5$) is selected from the group consisting of acetone, $C_1$–$C_3$ light alcohols, ethyl acetate, methylene chloride and mixtures thereof.

18. The process according to claim 17, wherein:
in step (a):
the raw material is selected from the group consisting of barks, branches and needles of said conifers, or mixtures thereof;
the organic solvent is selected from the group consisting of alcohols, halogenated hydrocarbons and mixtures of alcohols and halogenated hydrocarbons;

prior to carrying out step (b):
the biomass is precipitated in a basic medium consisting of a solution of a basic salt selected from the group consisting of sodium acetate, potassium acetate, sodium hydroxide and tris(hydroxymethyl) aminomethane;

in step (d):
the Paclitaxel-enriched phase obtained in step (c) is evaporated to dryness and dissolved in methanol.

19. The process according to claim 18, wherein:
in step (a):
the raw material is selected from the group consisting of barks, branches and needles of said conifers, or mixtures thereof;
the organic solvent is selected from the group consisting of alcohols, halogenated hydrocarbons and mixtures of alcohols and halogenated hydrocarbons;

in step (b):
the biomass is precipitated in an acidic medium consisting of a solution of an acid selected from the group consisting of hydrochloric, acetic and citric acids;
the acid is used in a concentration of between 10 mM and 50 mM per liter of solution; and
the pH of the solution is between 2 and 4; and prior to carrying out step (d):
the Paclitaxel-enriched phase obtained in step (c) is evaporated to dryness and dissolved in methanol.

* * * * *

UNITED STATES PATENT AND TRADEMARK OFFICE
CERTIFICATE OF CORRECTION

PATENT NO.    : 6,452,024 B1
DATED         : September 17, 2002
INVENTOR(S)   : Trung Bui-Khac et al.

It is certified that error appears in the above-identified patent and that said Letters Patent is hereby corrected as shown below:

<u>Title page,</u>
Item [30], Foreign Application Priority Data, please add
-- [30]  June 22, 1999 (CA) ................................2275980 --

Signed and Sealed this

Tenth Day of June, 2003

JAMES E. ROGAN
*Director of the United States Patent and Trademark Office*